US011399738B2

(12) United States Patent  
Korotko et al.

(10) Patent No.: US 11,399,738 B2  
(45) Date of Patent: Aug. 2, 2022

(54) VESSEL CALIPER

(71) Applicant: Accumed Radial Systems, LLC, Farmington Hills, MI (US)

(72) Inventors: Joseph R. Korotko, Livonia, MI (US); Ronan, Winter Garden, FL (US); Mauricio G. Cohen, Miami, FL (US)

(73) Assignee: Accumed Radial Systems, LLC, Farmington Hills, MI (US)

( * ) Notice: Subject to any disclaimer, the term of this patent is extended or adjusted under 35 U.S.C. 154(b) by 0 days.

(21) Appl. No.: 17/106,811

(22) Filed: Nov. 30, 2020

(65) Prior Publication Data

US 2021/0251515 A1 Aug. 19, 2021

Related U.S. Application Data

(60) Provisional application No. 62/972,910, filed on Feb. 11, 2020.

(51) Int. Cl.
| | |
|---|---|
| *A61B 5/107* | (2006.01) |
| *A61B 5/02* | (2006.01) |
| *A61M 25/02* | (2006.01) |
| *A61B 10/00* | (2006.01) |

(52) U.S. Cl.  
CPC ........ *A61B 5/1076* (2013.01); *A61B 5/02007* (2013.01); *A61B 2010/0093* (2013.01); *A61M 25/02* (2013.01)

(58) Field of Classification Search  
CPC .............. A61B 5/1076; A61B 5/02007; A61B 2010/0093; A61B 2090/061; A61M 25/02; A61M 2025/024; A61F 2/2496; G01B 3/20; G01B 3/28  
See application file for complete search history.

(56) References Cited

U.S. PATENT DOCUMENTS

| | | | |
|---|---|---|---|
| 5,690,645 A | 11/1997 | Van Erp | |
| 5,860,923 A * | 1/1999 | Lenker | A61B 5/02014 600/433 |
| 6,231,547 B1 * | 5/2001 | O'Hara | A61M 25/02 604/174 |
| 6,450,976 B2 | 9/2002 | Korotko et al. | |
| 7,776,017 B2 * | 8/2010 | Ponzi | A61M 25/02 604/180 |
| 2001/0039388 A1 | 11/2001 | Korotko et al. | |
| 2002/0151871 A1 * | 10/2002 | Gaiser | A61M 25/02 604/510 |
| 2010/0056958 A1 | 3/2010 | Ravi | |
| 2014/0121643 A1 | 5/2014 | McKinnis et al. | |

OTHER PUBLICATIONS

International Search Report and Written Opinion for International Patent Application No. PCT/US2021/017203 dated May 21, 2021.

* cited by examiner

*Primary Examiner* — Devin B Henson  
(74) *Attorney, Agent, or Firm* — Carlson, Gaskey & Olds, P.C.

(57) ABSTRACT

An example vessel caliper according to the present disclosure includes a scale having a first clamp, and a slider movable relative to the scale such that a length measurement can be determined, the slider having a second clamp. Each of the first and second clamps have a spring action jaw configured to capture a catheter assembly therebetween. An example method of using the vessel caliper is also disclosed.

23 Claims, 8 Drawing Sheets

VESSEL CALIPER

CROSS-REFERENCE TO RELATED APPLICATIONS

This application claims priority to U.S. Provisional Application Ser. No. 62/972,910 filed Feb. 11, 2020, which is hereby incorporated by reference herein in its entirety.

BACKGROUND

Certain medical procedures benefit from the ability to perform intra-vascular length measurements. For instance, catheterization procedures that address or treat artifacts inside blood vessels such as blockages may benefit from the ability to measure those artifacts.

SUMMARY

An example vessel caliper according to the present disclosure includes a scale having a first clamp, and a slider movable relative to the scale such that a length measurement can be determined, the slider having a second clamp. Each of the first and second clamps have a spring action jaw configured to capture a catheter assembly therebetween.

An example method of using a vessel caliper according to the present disclosure includes inserting a catheter assembly into a vessel of a patient via an access point, arranging a vessel caliper near the access point of a patient, the vessel caliper including a slider that is movable relative to a scale, each of the slider and the scale having a clamp with a spring action jaw, opening the spring action jaws, inserting a catheter assembly into the spring action jaws, closing the spring action jaws to capture the catheter assembly therein, and moving the slider relative to the scale to make a length measurement.

DETAILED DESCRIPTION

Figure 1:
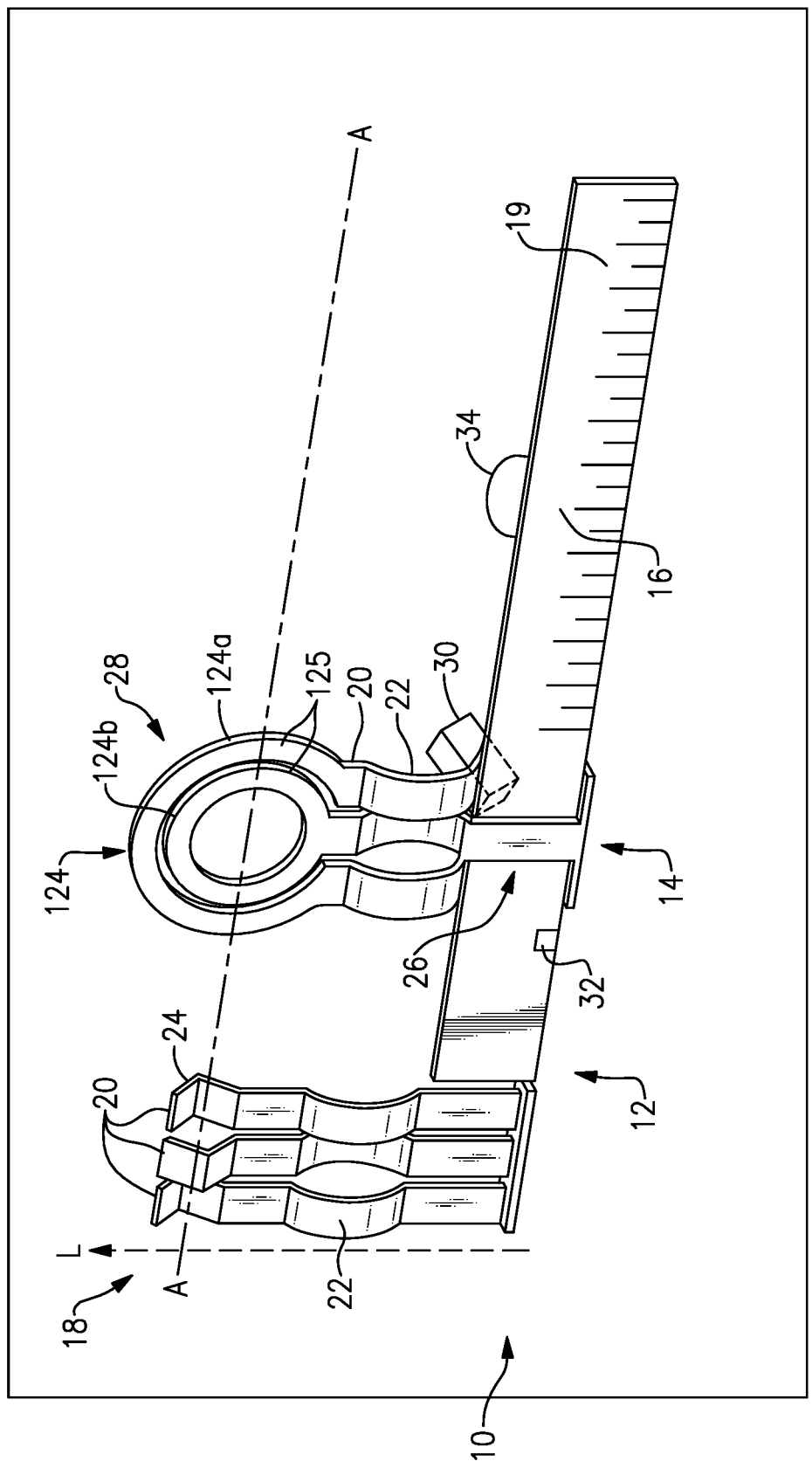
FIGS. 1-2 show an example vessel caliper with example clamps.
Figure 2:
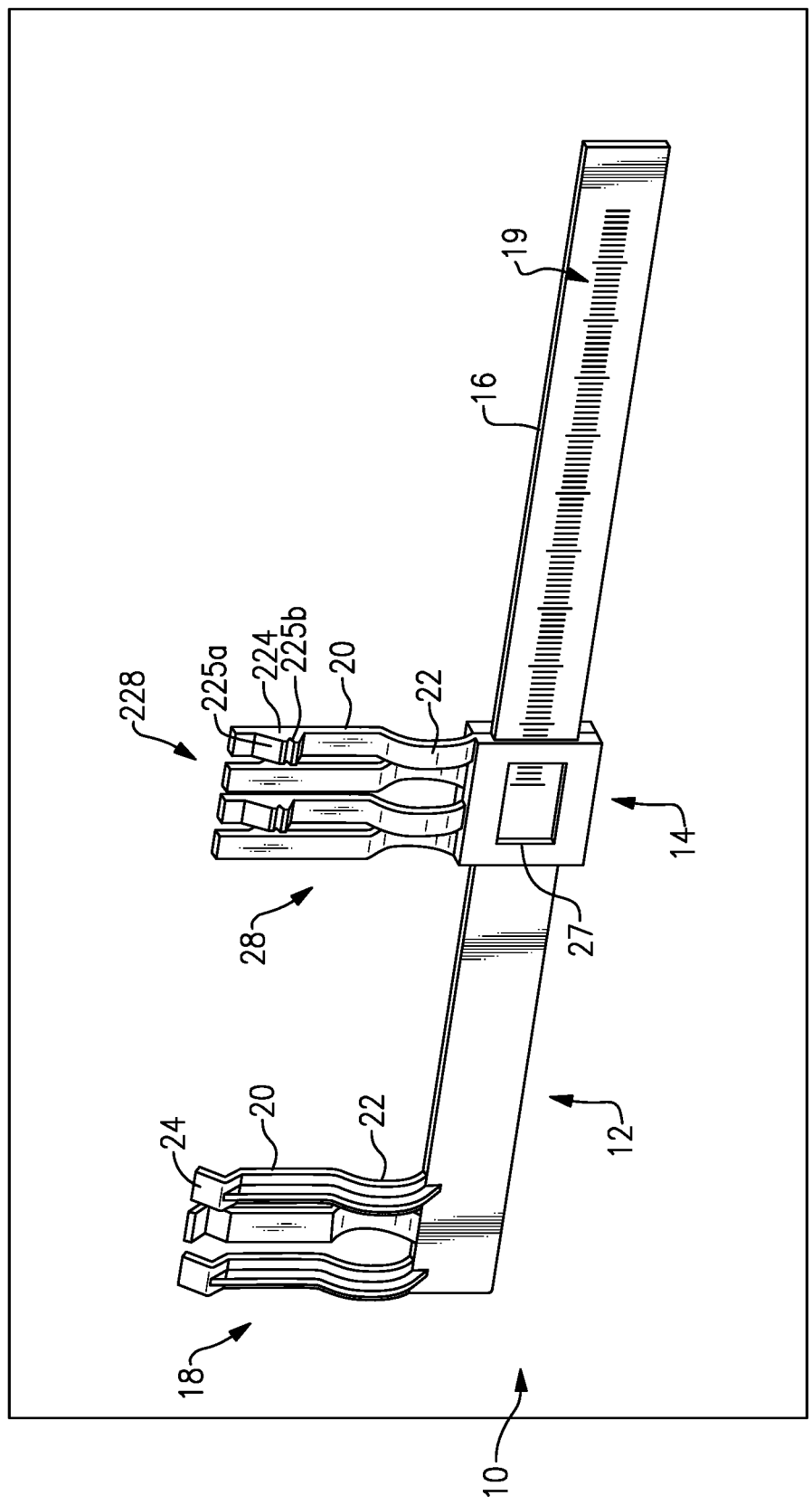

FIGS. 1 and 2 show an example vessel caliper 10. The vessel caliper 10 is configured to make intra-vascular measurements during certain medical procedures, such as a catheterization procedure, which will be discussed in more detail below. The vessel caliper 10 includes, in general, a scale 12 and a slider 14. The slider 14 is movable with respect to the scale 12.

The scale 12 and slider 14 could be made of any known polymeric material. In one example, the material of the scale 12 and/or the slider 14 includes a reflective or fluorescent material to facilitate visibility in low light situations.

The scale 12 includes a rod 16 and a clamp 18. The rod 16 includes a ruler or other markings 19 from which a length measurement can be determined. The markings could be printed, molded, or otherwise included in the rod 16. The clamp 18 is situated at a distal end of the rod 16. The clamp 18 is configured to capture one or more medical devices, such as a catheter assembly (discussed in more detail below). Various medical procedures may benefit from the ability to perform intra-vascular length measurements as the medical device is advanced into the body of a patient.

The clamp 18 could be any type of clamp, but generally includes a spring-action jaw. In one example, shown in FIG. 1, the clamp 18 includes one or more fingers 20 that together provide a spring. The fingers 20 each include a compression point 22, and the compression points 22 of each finger 20 are aligned with one another such that they can be simultaneously compressed. The compression points 22 can be, for instance, a rounded portion of the fingers 20, as in the example of FIG. 1, though other geometries are contemplated so long as they allow for compression. In general, the compression points 22 extend away from a longitudinal axis L of the fingers 20. The fingers 20 are flexibly connected to the rod 16 at their proximal ends so that the fingers 20 can flex with respect to the rod 16 upon the compression described above. In one example, the fingers 20 are integrally molded with the rod 16.

The flexible fingers 20 each also include a jaw 24 at its distal end. In the example of FIG. 1, the jaws 24 include an angled portion, which is configured to capture a medical device such as a catheter assembly. In other examples, the jaws 24 can have a different geometry, so long as the geometry enables the jaw to capture a medical device. For example, the geometry of the jaw can correspond to the geometry of the medical device.

The flexible fingers 20 are oriented in an alternating pattern. In the example of FIG. 1, of the three flexible fingers 20, the center finger 20 has a reversed orientation as compared to the outer fingers 20. That is, the center finger 20 has a jaw 24 that opens in an opposite direction from the jaws 24 of the outer fingers 20, and a compression point 22 that is compressible in an opposite direction from the compression points 22 of the outer fingers 20. In this way, simultaneous compression of the compression points 22 by a pinching motion causes the jaws 24 to move away from a central axis A, shown in FIG. 1. Release of the compression points 22 causes the jaws 24 to move towards the central axis A and trap a medical device therein. Thus, the medical device can be inserted or removed from the clamp 18.

Furthermore, the alternating orientation of the jaws 24 enhances the capturing of the medical device in the clamp 18 by securing the medical device from two opposing directions. In one example, the medical device is captured in the clamp 18 such that the medical device is still slidable with respect to the clamp 18. In another example, however, the medical device is captured in the clamp 18 such that the medical device is not slidable with respect to the clamp 18. In the latter case, the clamp 18 is configured to provide only a pressure sufficient to capture and secure the medical device but avoid damaging or collapsing it. Further, in some examples, the jaws 24 have an interior surface that is a slip-reduced surface, such as a rubberized, sticky, or textured surface, to inhibit the medical device from slipping/moving with respect to the notch jaws 24.

In the example of FIG. 1, there are three fingers 20, though in other examples, more or less fingers 20 could be used so long as they are oriented for the compression and trapping of a medical device as discussed above.

The slider 14 is slidable with respect to the rod 16. In the example of FIG. 1, the slider 14 includes an opening 26 which receives the rod 16 therein to enable the slider 14 to slide along the rod 16, though other arrangements are contemplated. The slider 14 could include a window 27 through which the markings 19 on the rod are visible, best seen in FIG. 2. In one example, the window 27 includes a magnifying element to assist viewing the markings 19. The slider 14 also includes a clamp 28. In one example, the clamp 28 is integrally molded with respect to the slider 14. The clamp 28 can be similar to or even the same as clamp 18. As with the clamp 18, the clamp 28 can capture a medical device such that it is slidable or not slidable with respect to the clamp 28. In the latter case, the clamp 28 is configured to provide only a pressure on the medical device sufficient to secure it but avoid damaging or collapsing it.

To that end, one example clamp 28, shown in FIG. 1, includes three fingers 20 with a compression point 22 like the clamp 18. The example clamp 28 includes a jaw 124 that is different from the jaws 24 of the clamp 18. The jaw 124 includes an outer portion 124a extending from and connecting the inner and outer fingers 20 and an inner portion 124b extending from the middle finger 20. The inner portion 124b generally tracks the shape of outer portion 124a, and fits inside portion 124a when compression points 22 are not compressed. Compression of the compression points 22 causes the inner and outer portions 124a, 124b to move in opposite directions away from the central axis A, and the at least one catheter can be received between the inner and outer portions 124a, 124b. Release of the compression points 22 causes the portions 124a, 124b to move towards one another so as to trap the medical device between the portions 124a, 124b. It should be understood that the circular shape of inner and outer portions 124a, 124b in FIG. 1 is only exemplary, and other shapes could be used as well. In one example, the circular shape serves as a finger loop to facilitate movement of the slider 14.

In one example, the portions 124a, 124b include a notch 125 to accommodate the medical device, which may help avoid damaging or collapsing the medical device when it is captured in the jaw 124. Still, the medical device is generally secure in the jaw 124, as discussed above, even without the notch 125.

In one example, the notch 125 includes a slip-reduced surface, such as a rubberized, sticky, or textured surface, to inhibit the medical device from slipping with respect to the notch 125.

FIG. 2 shows a vessel caliper 10 with another example clamp 228 for the slider 14. The clamp 228 is similar to the clamp 18. However, in this example, the clamp 228 includes four fingers 20 with compression points 22. As above, the fingers 20 have alternating orientations. Also as above, the fingers 20 each include a jaw 224. The jaws 224 each include a protrusion 225a with a notch 225b, and the notch is configured to receive the medical device, similar to the notch 125 discussed above. In the example, the protrusions 225a are triangular, though other geometries are contemplated.

In one example, one or both of the clamps 18 and 28/228 include a lock 30, shown schematically in FIG. 1. The lock 30 is configured to prevent compression of compression points 22 in certain circumstances. For instance, after insertion of a medical device into the clamp 18/28/228, the lock 30 could be engaged to prevent accidental compression of the compression points 22 and accidental loosening of the clamps 18/28/228 during a medical procedure. The lock 30 could include any known locking mechanism, such as opposed surfaces with serrated edges that interlock with one another, a clip, key/tab features, etc.

In one example, at least one of the slider 14/rod 16 include a zero-position lock 32, schematically shown in FIG. 1. The zero-position lock 32 is configured to hold the slider 14 in a zero-position on the rod 16, for instance, during capturing of a medical device in the clamp 28/228 on the slider 14. The zero-position lock 32 could be, for instance, a "seesaw" toggle or cantilever-type switch that either itself prevents movement of the slider 14 when engaged, or causes a tab or other structure to become engaged in order to prevent movement of the slider 14 when engaged.

In one example, the vessel caliper 10 includes a thumb wheel 34, shown schematically in FIG. 1, which is operable to move the slider 14 along the rod 16. The thumb wheel 34 could include tactile or audible "click" features which could correspond to specific length measurements. For instance, each tactile or audible click could correspond to a length of 5 mm.

In one example, the vessel caliper 10 may include electronic components that are configured to display length measurements.

Figure 3:
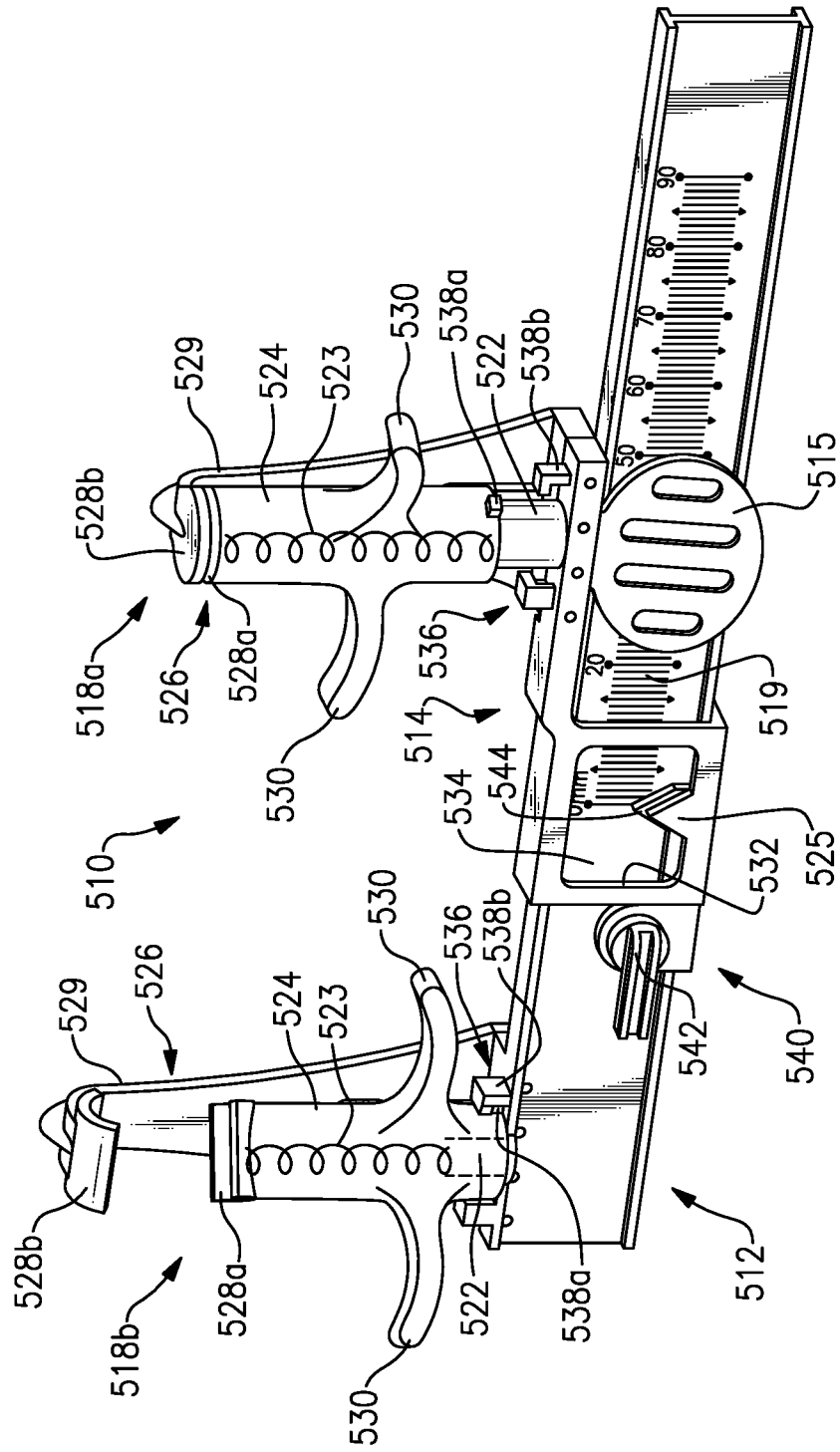
FIGS. 3-4 show another example vessel caliper with another example clamp.

FIG. 3 shows another example vessel caliper 510. It should be understood that the features described with respect to the vessel caliper 10 can also be used with the vessel caliper 510, and vice versa. Like the vessel caliper 10, the vessel caliper 510 includes, in general, a scale 512 and a slider 514. The slider 514 is movable with respect to the scale 512. The slider 514 may include a grip 515, which could have indentations therein that provide a reduced-slip surface.

The scale 512 and slider 514 could be made of any known polymeric material. In one example, the material of the scale 512 and/or the slider 514 includes a reflective or fluorescent material to facilitate visibility in low light situations.

The scale 512 includes a rod 516. The rod 516 includes a ruler or other markings 519 from which a length measurement can be determined. The markings 519 could be printed, molded, or otherwise included in the rod 516.

The vessel caliper 510 includes at least one clamp 518. The clamp 518 is configured to capture a medical device.

In this example, there are two clamps 518a/518b, though in other examples more or less clamps 518 could be used. More particularly, in this example, one clamp 518a is attached to or integral with the slider 514 while the other clamp 518b is attached to or integral with the scale 512. Thus one clamp 518a may be movable with respect to the other clamp 518b via movement of the slider 514 as discussed above. In this particular example, the first clamp 518a is situated at a proximal end of the slider 514 while the second clamp 518b is situated at a distal end of the scale 512.

The clamp 518a/518b could be any type of clamp, but in this example generally is a spring-action clamp. More particularly, in this example, the clamp 518a/518b includes a base 522 with a spring 523 attached thereto. A housing 524 is situated over the base 522 and is also connected to the spring 523. The housing 524/base 522 can be cylindrical, or can have another profile.

The clamp 518a/518b also includes a jaw 526 opposite the base 522. The jaw 526 includes a proximal portion 528a and a distal portion 528b opposed from the proximal portion 528a. The proximal portion 528a is connected to or integral with the housing 524. The distal portion 528b is supported by a support 529 which extends at least to, or past, the base 522. The support 529 could be connected to the base 522 or to the slider 514/scale 512 at a location near the base 522.

A medical device is receivable between the distal and proximal portions 528a/528b. The spring 523 biases the proximal portion 528a towards the distal portion 528b to hold the clamp 518a/518b is in a closed position and thereby capture the medical device between the distal and proximal portions 528a/528b.

The clamp 518a/518b also includes one or more levers 530. In the example shown, there are two levers 530, one on either side of the base 522. The lever(s) 530 can be depressed towards the slider 514/scale 512 to overcome the spring force of the spring 523 and thus the clamp 518a/518b can be opened, and the medical device can be removed from or re-placed in the clamp 518a/518b. In some examples, the lever(s) 530 can have a curved profile for an improved grip by a user.

In some examples, one or both of the distal and proximal portions 528a/528b can have a curved profile. In a particular example, the second clamp 518b has distal and proximal portions 528a/528b with curved profiles that correspond to a profile of a medical device configured to be held therein.

In one example, one or both of the clamps 518a/518b includes a lock 536. The lock 536 is operable to retain the clamp 518a/518b in an open position. For instance, the lock 536 can include a tongue feature 538a on the housing 524 which is receivable in a groove feature 538b in the scale 512 or slider 514 near the base 522. The housing 524 may be rotatable with respect to the base 522 so that the lock 536 can be engaged/disengaged.

In one example, one or both of the distal and proximal portions 528a/528b includes a slip-reduced surface, such as a rubberized, sticky, or textured surface, to inhibit the medical device from slipping with respect to the distal and proximal portions 528a/528b.

Figure 4:
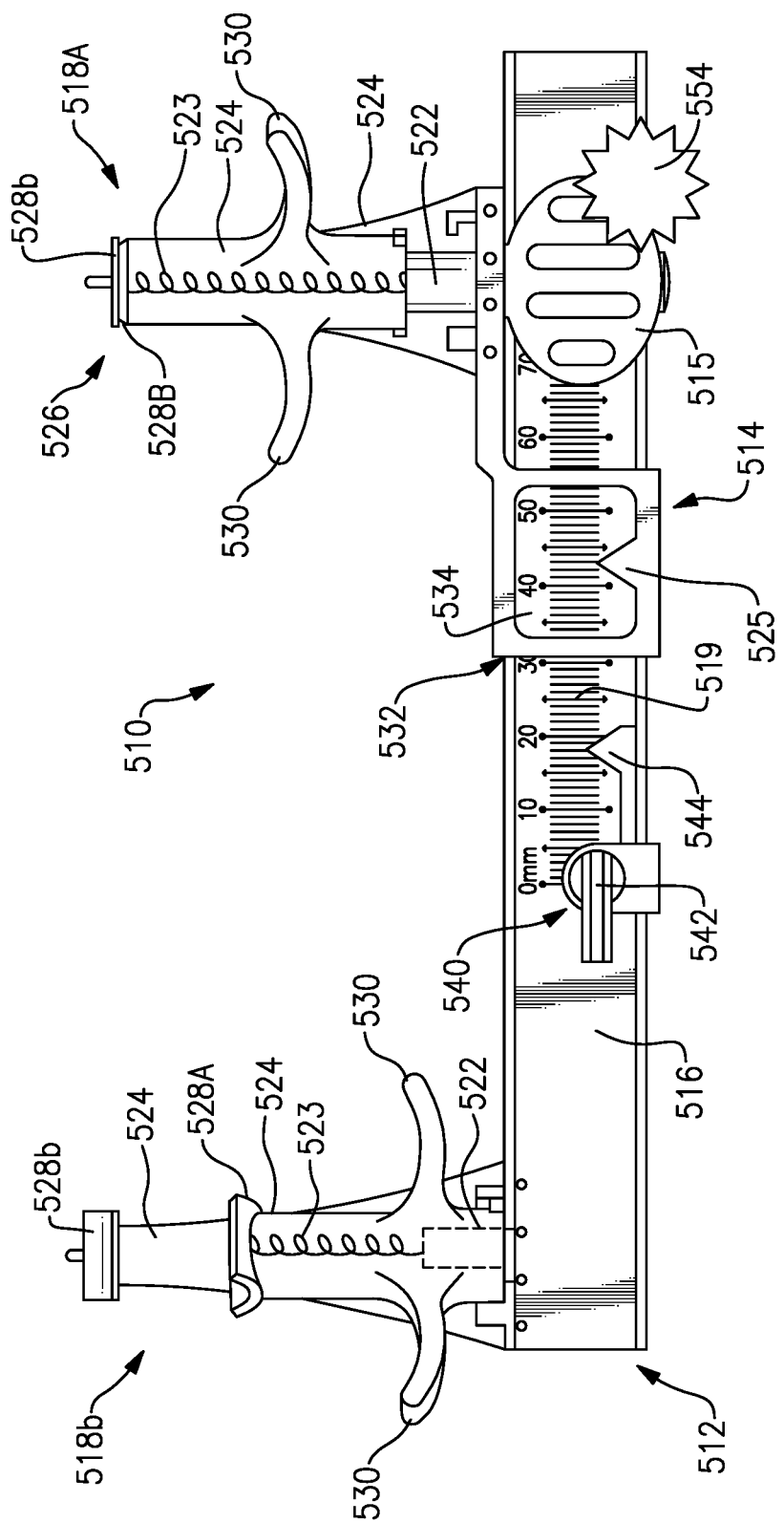

The slider 514 is slidable with respect to the rod 516. In the example of FIGS. 3-4, the slider 514 includes an opening 532 which receives the rod 516 therein to enable the slider 514 to slide along the rod 516, though other arrangements are contemplated. The slider 514 could include a window 534 through which the markings 519 on the rod 516 are visible. In one example, the window 534 includes a magnifying element to assist viewing the markings 519. The slider 514 can also include a pointer or arrow 525, in some examples, which can indicate a marking 519 that corresponds to a measurement.

The vessel caliper 510 can also include at least one marker 540, best seen in FIG. 4. The marker 540 is attached to the rod 516 and is slidable with respect to the rod 516. The marker 540 may have a marker lock 542. The marker lock 542 is configured to lock the marker 540 onto the rod 516 at a specific location of marking 519. The marker lock 542 may be in the form of a set-screw that is turned to activate and deactivate the marker lock 542. This is just one example form of a marker lock 542 and other designs are contemplated so long as the marker lock 542 retains the marker 540 with respect to the rod 516. The marker 540 also includes a pointer or arrow 544 which can be used to indicate a marking 519 that corresponds to a measurement. In one example, the marker 540 can slide on the rod 516 such that the pointer or arrow 544 can be situated behind the pointer or arrow 525 of the slider 514, as shown in FIG. 3. Thus the marker 540 allows for marking another measurement independent from the measurement marked with the slider 514 as discussed above.

Figure 5:
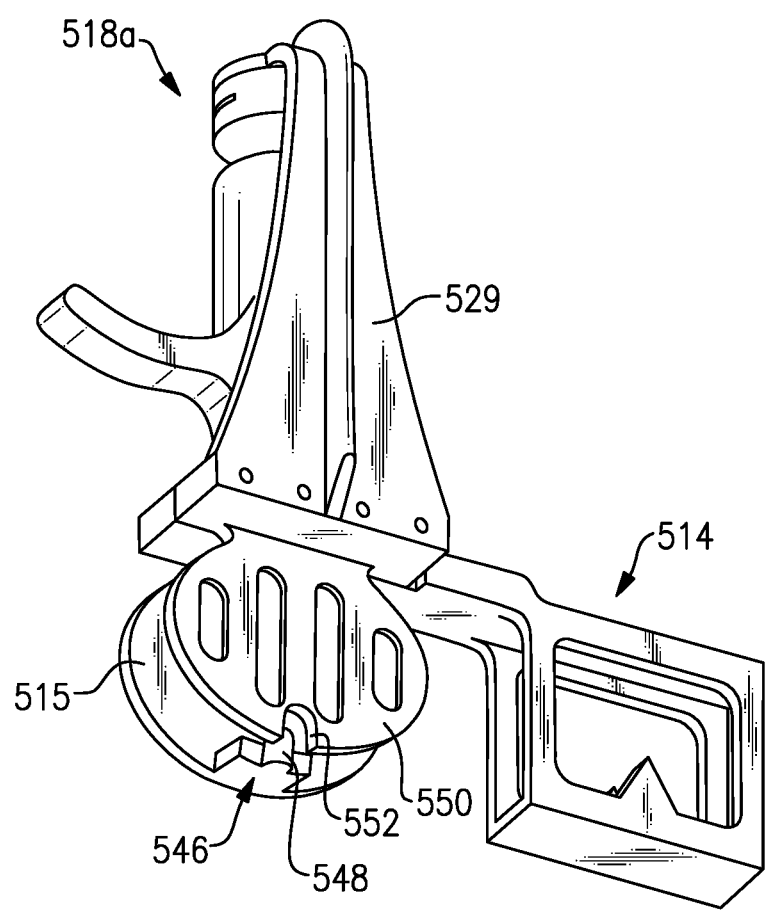
FIG. 5 shows a detail view of an example zero-position lock of the example vessel caliper.
Figure 6:
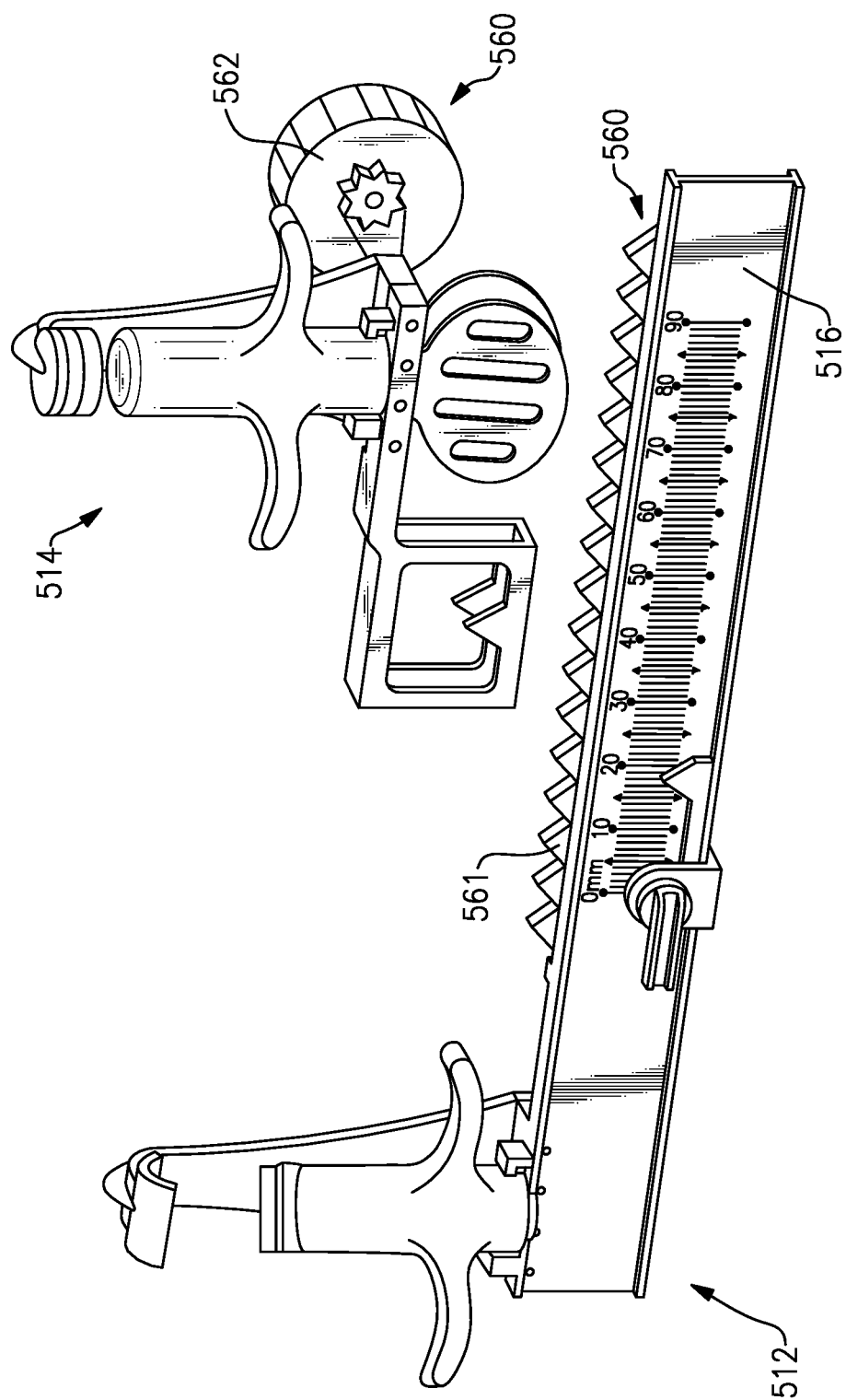
FIG. 6 shows a detail view of an example regulator of the example vessel caliper.

The vessel caliper 510 also may include a zero-position lock 546, in some examples. The zero position lock 546 is best shown in FIG. 5 and includes a tongue/groove lock feature, though other types of locks 546 are also contemplated. In this example, the grip 515 includes a tab 548. The support 529 includes a grip 550 that corresponds to the grip 515 such that the rod 516 would be sandwiched between the grip 515 and grip 550. The grip 550 includes an opening 552 configured to receive the tab 548, thereby locking the slider 514 onto the rod 516 in a desired position. Alternatively, the rod 516 includes an opening 552 configured to receive the tab 548, thereby locking the slider 514 onto the scale 512 in a desired position. For instance, the lock 546 could be used during capturing of a medical device in the clamp 518a/518b on the slider 514. In other examples, the zero-position lock 546 could be, for instance, a "seesaw" toggle or causes a tab or other structure to become engaged in order to prevent movement of the slider 514 when toggled. In a further example, the zero-positon lock 546 may have a design such that the zero-position lock 546 becomes automatically un-locked when an operator grasps the slider 514 at the start of a measurement. Grasping the grip 515 and the grip 550 simultaneously is one possible way in which automatically un-lock the zero-position lock 546. Other ways, such as manually unlocking the zero-position lock 546, are contemplated. The zero-position lock 546 would then be in the un-lock position while a measurement is being made. Still further, the zero-position lock 546 may have a design such that when the operator returns the slider 514 to the zero position on the scale 512, the zero-position lock 546 automatically activates and locks the slider 514 to the scale 512 by engaging the tab 548 with the opening 552, for example.

In one example, the vessel caliper 510 includes a thumb wheel 554, shown in FIG. 4. The thumb wheel 554 could be associated with the grip 515, as shown in the example of FIG. 4, but could also be associated with other parts of the slider 514. The thumb wheel 554 is operable to move the slider 514 along the rod 516. The thumb wheel 554 could include tactile or audible "click" features which could correspond to specific length measurements. For instance, each tactile or audible click could correspond to a length of 5 mm.

In one example, the vessel caliper 510 may include electronic components that are configured to display length measurements.

The vessel caliper 510 may include a regulator 560. The regulator 560 is configured to controllably move the slider 514 along the scale 512. The regulator 560 includes components that are integral with or attached to both the scale 512 and slider 514 to control their relative movement. As an example, the regulator 560 could have a rack-and-pinion gear design. In this example, the rack portion 561 of the regulator 560 would be integral with or attached to the scale 512, such as via the rod 516, and the pinion gear 562 would be integral with or attached to the slider 514, though the opposite configuration could also be used. The rack 561/pinion gear 562 interface to allow for the controlled movement and positioning of the slider 514 along the scale 512. For example, each of the teeth of the rack/pinion gear 561/562 may correspond to a specific amount of movement, such as 5 mm. In another example, the regulator 560 includes components of interfacing screw threads. One profile of a screw thread, such as a male thread profile, could be integral with the scale 512 and another interfacing screw thread profile, such as a female thread profile, could be integral with the slider 514. Assembly of the scale 512 and the slider 514 engages the interfacing screw threads. A dial similar to a turn knob could be integral to either of the interfacing screw thread profiles. Turning the dial activates motion of the interfacing screw threads and can thus cause controlled movement of the slider 514 along the scale 512.

The regulator 560 may have a movement indicator feature which could provide real-time feedback to the operator that the slider 514 is moving along the scale 512. The movement indicator may provide feedback at designated intervals. For example, the movement indicator feature may provide feedback every 5-mm of movement. The movement indicator feedback may be in the form of tactile feedback for the sensation of touch, or in the form of audio feedback for the sensation of sound, or both.

Figure 7:
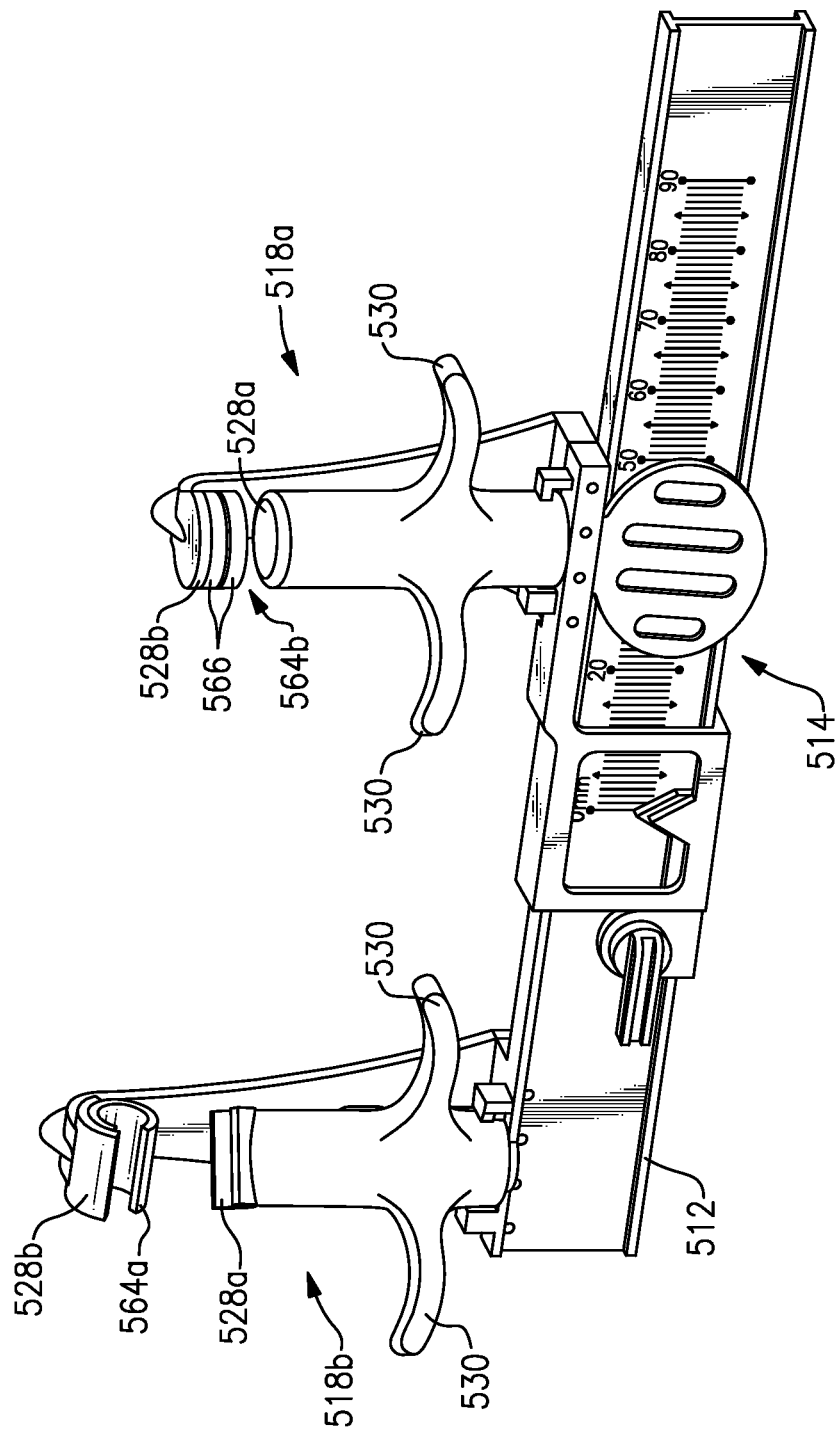
FIG. 7 shows the example vessel caliper of FIGS. 1-2 with inserts

FIG. 7 shows the vessel caliper 510 including an insert 564a/564b in each of the jaws 526 of each of the clamps 518a/518b, respectively. In this example, the inserts 564a/564b have a geometry/dimensions configured to interact with a portion of the medical device configured to be captured by the clamps 518a/518b. The inserts are located between the proximal/distal portions 528a/528b of the jaw 526, and may be connected to or integral with one of the proximal/distal portions 528a/528b of the jaw 526. Still, while the inserts 564a/564b assist in capturing the medical device in the clamps 518a/518b, the jaw 526 still participates in the capturing by providing additional pressure/security on the object via the spring-loaded nature of the jaw 526, as discussed above. The inserts 564a/564b may be the same or different from one another. In the example of FIG. 7, the inserts 564a/546b are different from one another, and each is configured to capture a portion of a catheter assembly 600, as shown in FIG. 8 and discussed in more detail below.

Figure 8:
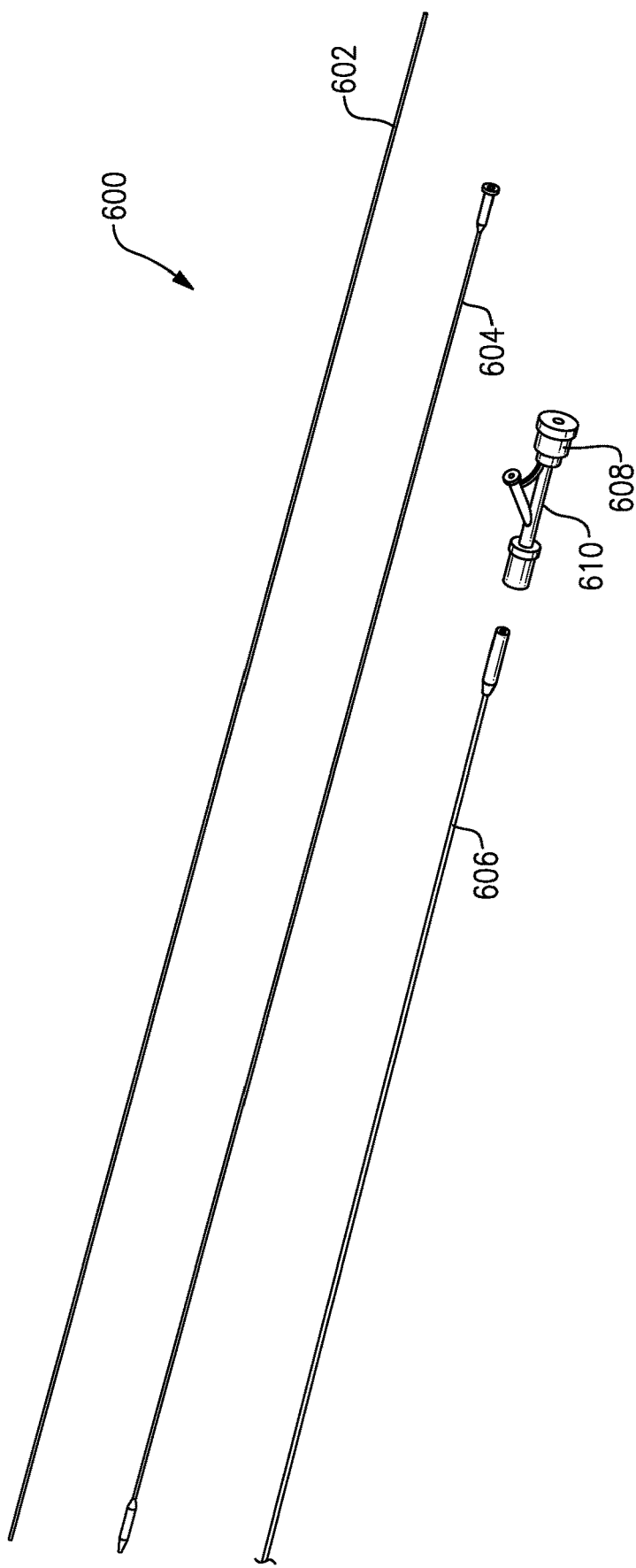
FIG. 8 shows an example catheter assembly for use with the example vessel caliper of FIGS. 1-2 or FIGS. 3-4.

One example medical device that could be captured by the vessel caliper 10/510 is a catheter assembly 600 as illustrated in FIG. 8 (which shows an exploded view of the catheter assembly 600). The catheter assembly 600 includes a guidewire 602, a working catheter 604 (which in this example is a balloon catheter, though other catheters such as a stent catheter can be used), a guide catheter 606, and a y-connector 608. The y-connector 608 is configured to interface with a distal end of the guide catheter 606. In operation, the y-connector 608 is connected to the proximal end of the guide catheter 606. The guidewire 602 and working catheter 604 are received inside the combined guide catheter 606 and the y-connector 608.

Returning to FIG. 7, in the example shown, the insert 564a, which is associated with the scale clamp 518b, is configured to interact with the y-connector 608. In this example, the insert 564a has a "c"-shape that has a geometry and dimensions such that it is configured to snap onto barrel portion 610 of the y-connector 608. The insert 564b, which is associated with the slide clamp 518a, is configured to interact with the guidewire 602 and working catheter 604. The guidewire 602 and working catheter 604 each have diameters that are considerably smaller than the barrel portion 610 of the y-connector 608. Therefore, an insert with a geometry/dimensions that correspond to the geometry/dimensions of the guidewire 602/working catheter 604 may be difficult to manufacture. In this example, the insert 564b includes malleable discs 566 which are configured to sandwich the guidewire 602 and working catheter 604 therebetween. The malleable discs may be foam discs, for instance. The malleable discs 566 may include a slip-resistant surface such as a rubberized surface which interacts with the guidewire 602/working catheter 604.

In operation, the catheter assembly 600 is inserted into a vessel of a patient via an access point. Typically, the guide catheter 606, which is already connected to the y-connector 608 is inserted first, followed by the guidewire 602 and the working catheter 604. The catheters are monitored by any imaging technique known in the art. The vessel caliper 10/510 is arranged near the access point, with the slider 14/514 arranged to indicate a "zero" measurement with respect to the scale 12/512. The clamps 18/28/228/518a/518b are then opened by depressing the levers 530 or compressing the compression points 22, as discussed above. In some examples, the clamps 18/28/218/518a/518b may be locked in the open position using the lock 536. The y-connector 608 is then inserted into the clamp 18/518b, and the clamp 18/518b is closed, and the guidewire 602/working catheter 604 are inserted into the clamp 28/228/518a and the clamp 28/228/518a is closed. At this stage, the slider 14/514 remains at a "zero," or first, position. Using the imaging technique, the working catheter 604/guidewire 602 and slider 14/514 are moved with respect to the scale 12/512, which remains stationary, to a desired, or second position within the vessel. Intravascular measurements can thus be made using the markings 19/519 to determine how far the slider 14/514/working catheters 604 was moved with respect to the scale 12/512.

In a particular example, the vessel caliper 10/510 can be used for intravascular measurements during an angioplasty procedure. An angioplasty procedure is used to repair a blockage in a vessel. An angioplasty procedure typically involves a balloon catheter as the working catheter 604 (the balloon is used to repair the blockage in various ways, as would be known in the art). The balloon catheter can include a radiopaque marker at its distal end that is visible based on the imaging technique that is used to monitor the procedure. During the procedure, the guidewire 602 is inserted into the vessel via the access point and advanced towards the blockage. The balloon catheter 604 is then inserted over the guidewire 602 and advanced towards the blockage. The balloon catheter 604 is advanced past the blockage and then aligned such that the radiopaque marker is situated at the distal end of the blockage. This alignment could be considered a first position of a measurement, or a zero-position of a measurement. This alignment would correspond to zero-position of the vessel caliper 10/510 that could be secured by the zero-position lock 546. Then, the vessel caliper 510 is situated adjacent the access point and captures the catheter assembly 600 as discussed above. The balloon catheter 604 is then pulled to the proximal end of the blockage by monitoring the location of the radiopaque marker via the imaging technique. The pulling causes the slider 14/514, which is securely attached to the balloon catheter 604 via the clamp 18/518a, as discussed above, to slide with respect to the scale 12/512, which remains stationary. When the radiopaque marker of the balloon catheter is at the proximal end of the blockage, the slider 14/514 is in a second position. The markings 19/519 can then be used to determine how far the slider 14/514 moved between the first and second positions, which corresponds to a length measurement of the blockage. Further, during a measurement, a user could temporarily stop moving the slider 514 along the scale 512 at a location somewhere between the first and second positions. The location of the temporary stop could be a point of interest to the user. The marker 540 could then be moved along the rod 516 portion of the scale 512 until the marker 540 abuts the slider 514 in order to mark the position of interest. The marker 540 could be locked at this location using the marker lock 542. The user could then resume the measurement by continuing to move the slider 514 along the scale 512. The marker 540 would remain where it was locked at the location of interest.

Although an embodiment of this disclosure has been explained, a worker of ordinary skill in this art would recognize that certain modifications would come within the spirit and scope of this invention.

The invention claimed is:

1. A vessel caliper, comprising:
   a scale having a first clamp; and a slider movable relative to the scale such that a length measurement can be determined, the slider having a second clamp;

wherein each of the first and second clamps have a spring action jaw with a first member comprising a base opposite the spring action jaw, a second member comprising a housing situated over the base such that the base is receivable in the housing and the housing is movable relative to the base, and a spring member comprising a spring connected to the base and the housing to bias the housing towards the jaw by spring force to capture a medical device therebetween, and at least one lever, the at least one lever operable to be depressed against the spring force to separate the housing and the spring action jaw to open the first or second clamp.

2. The vessel caliper of claim 1, wherein the housing includes the at least one lever.

3. The vessel caliper of claim 1, wherein the jaw of each of the first and second clamps includes a proximal portion and a distal portion configured to capture a medical device therebetween.

4. The vessel caliper of claim 3, further comprising a support supporting the distal portion, wherein the support extends from the distal portion to the base.

5. The vessel caliper of claim 3, wherein at least one of the proximal portion and the distal portion has a curved profile that corresponds to a profile of the medical device.

6. The vessel caliper of claim 3, wherein at least one of the proximal portion and the distal portion includes a slip-reduced surface.

7. The vessel caliper of claim 1, further comprising an insert inside at least one of the jaws of the first and second clamps, the insert configured to interface with a portion of the medical device.

8. The vessel caliper of claim 1, wherein at least one of the first and second clamps includes a clamp lock configured to lock the clamp in an open position.

9. The vessel caliper of claim 1, further comprising a regulator configured to control movement of the slider relative to the scale.

10. The vessel caliper of claim 1, further comprising a thumb wheel configured to move the slider relative to the scale.

11. The vessel caliper of claim 1, further comprising a zero-position lock configured to hold the slider in a zero-position with respect to the scale.

12. The vessel caliper of claim 1, further comprising a marker configured to slide with respect to the scale, the marker including a pointer configured to point to a marking on the scale that corresponds to a measurement.

13. The vessel caliper of claim 1, further comprising a zero-position lock configured to lock the slider at a zero-position with respect to the scale.

14. The vessel caliper of claim 1, wherein the medical device is a catheter assembly.

15. A method of using a vessel caliper, comprising:
inserting a catheter assembly into a vessel of a patient via an access point;
arranging a vessel caliper near the access point of a patient, the vessel caliper including a slider that is movable relative to a scale, each of the slider and the scale having a clamp with a spring action jaw, the spring action jaw having a first member comprising a base opposite the spring action jaw, a second member comprising a housing situated over the base such that the base is receivable in the housing and the housing is movable relative to the base, and a spring member comprising a spring connected to the base and the housing to bias the housing towards the jaw by a spring force;
opening the spring action jaws by depressing a lever against the spring force in the spring action jaws such that the housing is separated from the spring action jaw;
inserting the catheter assembly into the spring action jaws;
closing the spring action jaws to capture the catheter assembly therein by releasing the lever such that the spring force biases the housing towards the spring action jaw; and
moving the slider relative to the scale to make a length measurement.

16. The method of claim 15, wherein the slider is locked in a zero-position with respect to the scale prior to the step of opening the spring action jaws.

17. The method of claim 16, further comprising the step of grasping the vessel caliper prior to the moving step, and wherein the grasping automatically unlocks the slider from the zero-position.

18. The method of claim 15, further comprising inserting the catheter assembly into at least one insert situated in at least one of the spring action jaws prior to the step of closing the spring action jaws.

19. The method of claim 18, wherein the at least one insert includes a first insert in the slider spring action jaw and a second insert the scale spring action jaw, and further comprising inserting a y-connector of the catheter assembly into the second insert and inserting a working catheter into the first insert.

20. The method of claim 15, further comprising controlling movement of the slider via a regulator.

21. The method of claim 15, wherein the slider is moved relative to the scale via a thumb wheel.

22. The method of claim 15, wherein the length measurement corresponds to a length of a blockage in the vessel of the patient.

23. The method of claim 15, further comprising marking a measurement with a marker.

* * * * *